United States Patent [19]
Albrecht et al.

[11] 4,047,932
[45] Sept. 13, 1977

[54] HERBICIDAL AGENTS

[75] Inventors: Konrad Albrecht, Fischbach, Taunus; Peter Langeluddeke, Diedenbergen, Taunus; Hans Schumacher, Weilbach, Taunus; Friedhelm Schwerdtle, Frankfurt am Main, all of Germany

[73] Assignee: Hoechst Aktiengesellschaft, Frankfurt am Main, Germany

[21] Appl. No.: 583,514

[22] Filed: June 4, 1975

[30] Foreign Application Priority Data

June 6, 1974 Germany .............................. 2427270

[51] Int. Cl.² .............................................. A01N 9/20
[52] U.S. Cl. ....................................... 71/108; 71/111; 71/116

[58] Field of Search .......................... 71/108, 116, 111

[56] References Cited

U.S. PATENT DOCUMENTS

| | | | |
|---|---|---|---|
| 3,938,984 | 2/1976 | Fischer | 71/111 X |
| 3,954,442 | 5/1976 | Becker et al. | 71/116 X |

Primary Examiner—Lewis Gotts
Assistant Examiner—Catherine L. Mills
Attorney, Agent, or Firm—Curtis, Morris & Safford

[57] ABSTRACT

Compositions containing (I) chlorophenoxy-phenoxy-α-propionic acid (esters) and (II) 3-methoxy-carbonylaminophenyl-N-(3'-methylphenyl)-carbamate as active ingredients are used as synergistic herbicides against grassy and broad-leaf weeds.

5 Claims, No Drawings

HERBICIDAL AGENTS

The present invention provides herbicidal preparations containing as active ingredients mixtures of compounds of the formula

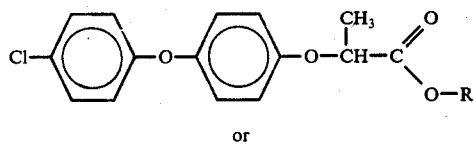

or

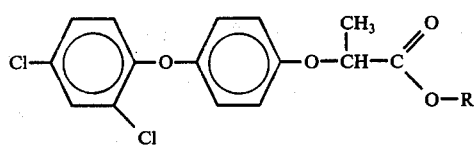

wherein R is hydrogen or an alkyl group having from 1 to 6 carbon atoms, and 3-methoxy-carbonylaminophenyl-N-(3'-methylphenyl)-carbamate of the formula

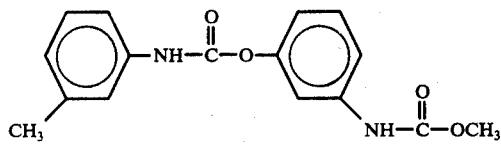

in combinaton with usual formulation auxiliaries.

The compounds of the formulae I and II are known from German Offenlegungsschrift No. 2,223,894. They have an excellent activity against a series of economically important grassy weeds such as annual blackgrass (*Alopecurus myosuroides*), wild oat (*Avena fatua*), barnyard grass (*Echinochloa crusgalli*), crabgrass (*Digitaria sanguinalis*), foxtail millet (*Setaria viridis* and *Setaria lutescens*), but they are not efficient against broad-leaved (dicotyledonous) weeds. They are used especially after emergence of said weeds.

The compound of formula III is also known e.g. from German Offenlegungsschrift No. 1,567,151. The compound, which is known under its generic name Phenmedipham, may be used for combating dicotyledonous weeds, preferably in sugar beets, when sprayed after emergence of the plants.

The mixtures of the invention suprisingly show a pronounced synergistic activity, especially for combating grasses in post-emergence treatment and in concentrations where one or both components only have an unsatisfactory effect.

The weight proportions of the active components may vary within wide limits. Combinations may be used, for example, containing from 0.1 to 5 parts by weight of compounds A and/or B per one part by weight of compound C. The weight proportion to be chosen in each particular case primarily depends on the weed collective spectrum to be combated and on the development stage of the weed species. The preferred weight proportions of A:B and/or A:C are in the range of from 0.15:1 to 2.5:1.

The herbicidal mixtures according to the invention may be used in the form of wettable powders, emulsifiable concentrates or dusting powders and may contain usual formulation auxiliaries such as wetting agents, adhesives, dispersing agents, solid or liquid inert carriers as well as grinding auxiliaries or solvents.

Carriers to be used are mineral substances as aluminum silicates, alumina, kaolin, chalks, siliceous chalk, and talcum, especially because of their absorbing capacity for preparations of type A or B, furthermore kieselgur or hydrated silicic acid. Suitable carriers for liquid preparations are all commonly used suitable organic solvents such as toluene, xylene, diacetone alcohol, isophorone, benzines, paraffin oils, dioxan, dimethyl formamide, dimethylsulphoxide, ethyl acetate, butyl acetate, tetrahydrofuran, chlorobenzene etc.

Suitable adhesives are cellulose products, partially hydrolyzed polyvinyl acetates, alcohols or pyrrolidones.

Examples of suitable wetting agents are non ionic emulsifiers such as oxethylated alkyl phenols as well as sodium salts of alkylarylsulfonic acids and alkylarylsulfuric acids, moreover sodium alkyl polyglycol ether sulfates or soaps.

As dispersing agents there may be used cell pitch (salts of sulfite waste liquor), sodium salts of alkylnaphthalenesulfonic acids as well as sodium salts of condensation products of formaldehyde with cresol and oxynaphthalene-disulfonic acids.

Suitable grinding auxiliaries are mineral or organic salts such as sodium sulfate, ammonium sulfate, sodium carbonate, sodium bicarbonate, sodium thiosulfate, sodium stearate or sodium acetate.

The herbicides according to the invention generally contain from 2 to 60%, preferably from 20 to 50% of the active substances A and/or B and C. The active ingredients in the formulation may also be in admixture with further known active substances.

The following examples illustrate the invention.

FORMULATION EXAMPLES:

Example 1

A wetting powder was prepared as follows: A liquid ester A or B was absorbed on finely dispersed silicic acid. Compound C and the formulation auxiliaries were ground on rapidly operating disk attrition of blowing mills and added to A. Both were then mixed and ground in a slowly operating cross beater mill to yield the desired wetting powder combination. The following composition was prepared in the above manner:

| | |
|---|---|
| 15.0 parts by weight | of the isobutyl ester of compound A |
| 30.0 parts by weight | of compound C |
| 10.0 parts by weight | of the sodium salt of a condensation product of cresol oxynaphthalene-disulfonic acid with formaldehyde |
| 6.0 parts by weight | of alkylnaphthalene-sulfonic acid sodium salt |
| 0.5 parts by weight | of soap |
| 3.5 parts by weight | of kaolin |
| 5.0 parts by weight | of sodium bicarbonate |
| 30.0 parts by weight | of finely dispersed silicic acid |
| 100.0 | |

Example 2

A wetting powder was prepared according to example 1 with the following components:

| | |
|---|---|
| 20.0 parts by weight | of the methyl ester of component B |
| 30.0 parts by weight | of compound C |
| 8.0 parts by weight | of the sodium salt of a condensation product of cresol and oxynaphthalene-disulfonic acid with formaldehyde |

-continued

| | |
|---|---|
| 0.5 parts by weight | of soap |
| 6.5 parts by weight | of alkyl-naphthalene sulfonic acid sodium salt |
| 5.0 parts by weight | of sodium bicarbonate |
| 30.0 parts by weight | of finely dispersed silicic acid |
| 100.0 | |

Example 3

An emulsifiable concentrate was obtained by formulating both active substances according to the following recipe:

| | |
|---|---|
| 7.5 parts by weight | of the isobutyl ester of compound A |
| 15.0 parts by weight | of compound C |
| 4.0 parts by weight | of calcium salt of dodecyl-benzene-sulfonic acid |
| 3.0 parts by weight | of triisobutyl-phenol-polyglycol ether |
| 2.0 parts by weight | of oleyl alcohol-polyglycol ether |
| 68.5 parts by weight | of isophorone |
| 100.0 | |

Example 4

Another emulsifiable concentrate was obtained by mixing the following components:

| | |
|---|---|
| 25.0 parts by weight | of the methyl ester of component B |
| 10.0 parts by weight | of compound C |
| 5.0 parts by weight | of dodecylbenzene-sulfonic acid calcium salt |
| 8.0 parts by weight | of castor-oil-polyglycol ether |
| 2.0 parts by weight | of oleyl alcohol-polyglycol ether |
| 50.0 parts by weight | of isophorone |
| 100.0 | |

BIOLOGICAL EXAMPLES

Example 1

In a green-house test compounds of type A and B were used along as well as in admixture with compound C after emergence of the plants. Table 1 shows the results obtained. It can be seen therefrom that compounds of type A and B had a good activity against the weeds used, whereas compound C was not or nearly not active. The activity of combinations A + C and b + C in many cases surpassed that of the compounds of type A and B used alone in equal concentration.

Similar results were obtained when using the butyl, propyl or hexyl esters of type A and B compounds. Notable variations could not be observed.

Example 2

Plots of a sugar beet field contaminated with annual blackgrass were sprayed with different preparations alone or in combination with one another, when the annual blackgrass had already developed 5 to 6 leaves and started to tiller.

The evaluation 4 weeks after treatment showed the following results: (cf. Table II).

An activity of the compound A against annual blackgrass at a dosage rate of 0.25 and 0.50 kg/ha could be observed, but was not satisfactory. An addition of compound C drastically improved the activity, although this compound alone was inefficient against annual blackgrass. This proves the synergistic effect of the combination. The sugar beet was not damaged.

TABLE I

Pot test with weed grasses in the green-house; dosage rates in kg/ha of A.S. (A.S. active substance); post-emergence treatment; efficiency expressed in % degree of damages

| dosage rates | | | activity against | | | |
|---|---|---|---|---|---|---|
| compound A (isobutyl ester) | compound B (methyl ester) | compound C | annual blackgrass | wild oat | barnyard grass | foxtail millet |
| 0 | 0 | 1.0 | 20 | 0 | 10 | 0 |
| 2.5 | | 0 | — | | — | 84 |
| 1.25 | | 0 | — | | — | 73 |
| 0.62 | | 0 | 83 | | 75 | 63 |
| 0.31 | | 0 | 49 | | 65 | — |
| 0.15 | | 0 | 8 | | 45 | — |
| 2.5 | | 1.0 | — | | — | 95 |
| 1.25 | | 1.0 | — | | — | 85 |
| 0.62 | | 1.0 | 94 | | 85 | 75 |
| 0.31 | | 1.0 | 89 | | 80 | — |
| 0.15 | | 1.0 | 84 | | 65 | — |
| | 2.5 | 0 | — | | — | 73 |
| | 1.25 | 0 | — | | — | 65 |
| | 0.62 | 0 | 68 | | 80 | 55 |
| | 0.31 | 0 | 41 | | 73 | — |
| | 0.15 | 0 | 0 | | 35 | — |
| | 2.5 | 1.0 | — | | — | 93 |
| | 1.25 | 1.0 | — | | — | 81 |
| | 0.62 | 1.0 | 78 | | 90 | 68 |
| | 0.31 | 1.0 | 68 | | 85 | — |
| | 0.15 | 1.0 | 57 | | 55 | — |

TABLE II

Field test with sugar beet and annual blackgrass; dosage rates in kg/ha of A.S.; post emergence treatment; efficiency expressed in % degree of damage

| dosage rates | | activity against | |
|---|---|---|---|
| compound A as isobutyl ester | compound C | annual blackgrass | sugar beet |
| 0 | 0.94 | 0 | 0 |
| 0.25 | 0 | 75 | 0 |
| 0.25 | 0.94 | 90 | 0 |
| 0.50 | 0 | 85 | 0 |
| 0.50 | 0.94 | 95 | 0 |
| 0.75 | 0 | 95 | 0 |
| 0.75 | 0.94 | 98 | 0 |

Example 3

Plots of a sugar beet field contaminated with foxtail millet (Setaria viridis and Setaria lutescens) were treated with various dosages of the compounds A and B alone or in combination with C. The weed grasses had developed 3 to 4 leaves. Table III shows the results obtained.

TABLE III

Field test with sugar beets and foxtail millet; dosage rates in kg/ha of A.S.; post-emergence treatment; activity expressed in % degree of damage

| dosage rates | | | activity against | |
|---|---|---|---|---|
| compound A as isobutyl ester | compound B as methyl ester | compound C | foxtail millet | sugar beet |
| 0 | 0 | 0.94 | 10 | 0 |
| 0.75 | 0 | 0 | 75 | 0 |
| 1.0 | 0 | 0 | 85 | 0 |
| 0.75 | 0 | 0.94 | 95 | 0 |
| 1.0 | 0 | 0.94 | 100 | 0 |
| 0 | 0.375 | 0 | 60 | 0 |
| 0 | 0.75 | 0 | 80 | 0 |
| 0 | 0.375 | 0.94 | 95 | 0 |
| 0 | 0.75 | 0.94 | 99 | 0 |

When using compound C alone practically no activity could be observed, whereas the activity of mixture A + C and B + C was better than that of B or A used alone.

Example 4

In a further pot test mixtures of A + C or B + C according to the invention were tested against sugar beets and a series of weed grasses (annual blackgrass and wild oat) and dicotyledonous weeds frequently found in sugar beet fields, in order to determine whether the combination may also be used against combinations of mono- and dicotyledonous weeds. (results cf. Table IV).

TABLE IV

Pot test with sugar beets, weed grasses and broad-leaf weeds; post-emergence treatment; dosage rates in kg/ha of A.S.; activity expressed in % degree of damage

| plant species | preparations and dosage rates | | | | |
|---|---|---|---|---|---|
| | C 0.94 | A 0.31 | A + C 0.31 + 0.94 | B 0.62 | B + C 0.62 + 0.94 |
| sugar beet | 0 | 0 | 0 | 0 | 0 |
| weed grasses: | | | | | |
| wild oat | 0 | — | — | 97 | 100 |
| annual blackgrass | 0 | 100 | 100 | — | — |
| dicotyledonous weeds: | | | | | |
| chickweed | 100 | 0 | 100 | 0 | 100 |
| wild camomile | 95 | 0 | 95 | 0 | 100 |
| redshank | 85 | 0 | 90 | 0 | 85 |
| further species[*)] | | | | | |

[*)]mixture of: small nettle, black nightshade and penny cress

The results obtained with the weed grasses chickweed (*Stellaria media*) wild camomile (*Matricaria chamomilla*), redshank (*Polygonum persicaria*), small nettle (*Urtica urens*), black nightshade (*Solanum nigrum*) and penny cress (*Thlaspi arvense*) demonstrate that the good activity of compound C against dicotyledonous species is not considerably improved by combining it with compounds of type A or B. When using the combination A + C annual blackgrass could be additionally destroyed and, when using the combination B + C, also wild oat.

Sugar beets were not damaged by any of said preparations or mixtures of preparations.

What is claimed is:

1. A herbicidal preparation comprising, as the active ingredient, a herbicidally effective amount of a mixture of 1.5 to 5 parts by weight of a compound selected from the group of compounds of the formulas

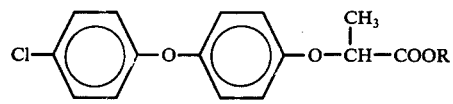

and

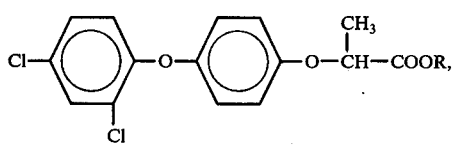

wherein R is hydrogen or alkyl having 1 to 6 carbon atoms, and 1 part by weight of 3-methoxy-carbonylaminophenyl-N-(3'-methylphenyl)-carbamate of the formula

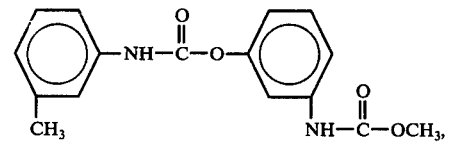

in combination with formulation auxiliaries.

2. A preparation as in claim 1 containing compound A, wherein R is isobutyl, with compound C.

3. A preparation as in claim 1 containing compound B, wherein R is methyl, with compound C.

4. The method of combatting weeds in crop plants which comprises applying thereto a preparation as in claim 1.

5. The method as in claim 4 wherein said crop plant is sugar beets.

* * * * *